United States Patent [19]
Hiroya

[11] Patent Number: 5,235,965
[45] Date of Patent: Aug. 17, 1993

[54] VIDEO ENDOSCOPE

[75] Inventor: Jun Hiroya, Tokyo, Japan

[73] Assignee: Olympus Optical Co., Ltd., Tokyo, Japan

[21] Appl. No.: 655,693

[22] Filed: Feb. 15, 1991

[30] Foreign Application Priority Data

May 2, 1990 [JP] Japan .................... 2-116115

[51] Int. Cl.5 .............................. A61B 1/06
[52] U.S. Cl. ................................... 128/6
[58] Field of Search .......................... 128/4, 6

[56] References Cited

U.S. PATENT DOCUMENTS

| | | | |
|---|---|---|---|
| 4,646,721 | 3/1987 | Arakawa | 128/6 |
| 4,784,144 | 11/1988 | Ono et al. | 128/634 |
| 4,807,597 | 2/1989 | Tsuno et al. | 128/6 |
| 4,942,867 | 7/1990 | Takahashi et al. | 128/6 |

FOREIGN PATENT DOCUMENTS

63-148225  6/1988  Japan .
1-265934  10/1989  Japan .

Primary Examiner—Gene Mancene
Assistant Examiner—Cindy A. Cherichetti
Attorney, Agent, or Firm—Armstrong, Westerman, Hattori, McLeland & Naughton

[57] ABSTRACT

A video endoscope provided in the insertable tip in parallel with an imaging apparatus and a treating instrument channel through which a laser treating instrument can be inserted and provided with a light intercepting part so that a leaking light of the laser treating instrument inserted through the treating instrument channel as well as reflected laser light may not enter the light receiving part of the imaging device through the other course than the optical course leading to the light receiving part of the imaging device through the image forming optical system from the observing window.

18 Claims, 6 Drawing Sheets

VIDEO ENDOSCOPE

BACKGROUND OF THE INVENTION

1. Field of the Invention

This invention relates to a video endoscope provided at the tip of the insertable part in parallel with an imaging apparatus and a treating instrument channel through which a laser treating instrument can be inserted.

2. Related Art Statement

This kind of video endoscope has an elongated flexible part, a bendable part and rigid tip part connected sequentially to this flexible part at the tip to form an insertable part, has an operating part connected to this insertable part at the rear end and a flexible: universal cord extended sidewise from this operating part and is provided in the above-mentioned operating part with a treating instrument inserting port communicating with the treating instrument channel provided in the above mentioned operating part. Also, the above mentioned video endoscope is provided at the tip of the insertable part in parallel with an imaging apparatus including an observing window, image-forming optical system and solid state imaging device, a treating instrument channel through which a treating instrument is to be passed and an illuminating optical system-- including an illuminating window and light guide fibers for illuminating a part to be inspected. Also, this endoscope is provided in the treating channel with a channel tube.

In the case of making a laser therapy by using such video endoscope, a laser treating instrument (laser probe) is inserted through the treating instrument inserting port and is directed at the tip to a desired part, for example, by bending the bendable Part and the part is imaged by the imaging apparatus and is laser-cauterized while the image is being observed in a monitor.

Now, there has been a problem that, in the case of the above mentioned laser-cauterization, a reflected laser light of the laser light radiated from the laser probe tip will enter the imaging apparatus through the observing window provided in the insertable part tip of the video endoscope and will be depicted in the monitor and the part of the object to be inspected will become hard to see.

In order to cope with this problem, there is suggested in Japanese patent applications laid open Nos. 148225/1988 and 265934/1985 a prior art wherein, in order to prevent a reflected laser light from entering an imaging device, an optical system leading to the imaging device is provided with an optical filter intercepting a laser light but transmitting a visible light.

However, in the above described prior art example, the laser light entering through the observing window at the insertable part tip can be coped with but the laser light entering the imaging device through the other course than the course leading to the imaging apparatus from the observing window can not be coped with.

That is to say, in the video endoscope, there is a disadvantage that, when the bendable part provided in the insertable part is bent, the laser probe will also bend, a laser light leaking from the laser probe, for example, in the bent part or a laser light emitted from the laser probe tip, is reflected and enters the treating instrument channel from the outlet opening leaking on the imaging apparatus side out of the peripheral wall of the treating instrument channel and will enter the imaging device, which causes the monitor image to become black and a produce flare or blooming.

OBJECTS AND SUMMARY OF THE INVENTION

An object of this invention is to provide a video endoscope whereby, when therapy utilizes laser treating instrument so that laser light leaking from the laser treating instrument inserted through the treating instrument channel as well as reflected laser light may not enter the light receiving part of the imaging device through a course other than the optical course leading to the light receiving part of the imaging device through the image forming optical system, from the observing window. As a result, the endoscope image formed by the imaging apparatus will not be obstructed, that is, the monitor image will not become black or produce a flare or blooming.

Another object of this invention is to provide a video endoscope which can be realized with existing component members without using an exclusive light shielding member or with a simple formation even if an exclusive light shielding member is used.

The video endoscope of this invention is provided at the tip of the insertable part in parallel with an imaging apparatus including an observing window, image forming optical system and imaging device and a treating instrument channel through which a laser treating instrument can be inserted and is provided with a light intercepting means for intercepting light so that laser light leaking from the laser treating instrument inserted through the above-mentioned treating instrument channel as well as a reflected laser light may not enter the light receiving part of the imaging device through a course other than the optical course leading to the light receiving part of the imaging device through the image forming optical system from the above-mentioned observing window.

The other features and advantages of this invention will become apparent enough with the following explanation.

BRIEF DESCRIPTION OF THE DRAWINGS

FIGS. 2 to 4 relate to the first embodiment of the present invention.

FIGS. 5 to 7 relate to the second embodiment.

FIGS. 8 and 9 relate to the third embodiment.

DETAILED DESCRIPTION OF THE PREFERRED EMBODIMENTS

Figure 1:
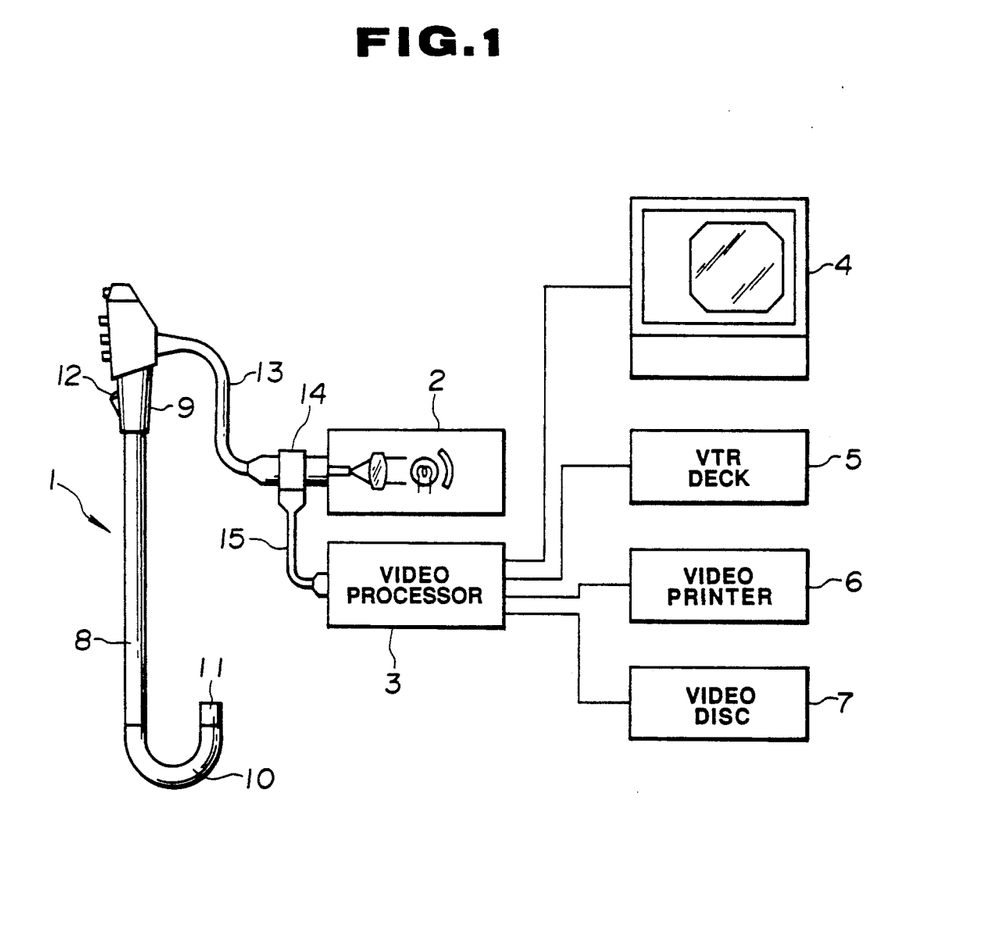
FIG. 1 is a formation diagram showing the whole of an example video endoscope apparatus to which a video endoscope of the present invention is applied.

As shown in FIG. 1, the endoscope apparatus for example, comprises a video system endoscope 1, a light source apparatus 2 and video processor 3 to which this endoscope 1 is connected and a monitor 4, VTR deck 5, video printer 6 and video disc 7, respectively, connected to the above mentioned video processor 3.

The above mentioned endoscope 1 has an elongate flexible insertable part 8, an operating part 9 connected to the insertable part 8 at the rear end and a bendable part 10 and rigid tip 11 connected sequentially to a flexible tube at the tip on the above mentioned insertable part 8 side. The above-mentioned operating part 9 is provided with a treating instrument inserting port 12 communicating with the treating instrument channel provided within the above mentioned insertable part 8. A flexible universal cord 13 is extended sidewise from the above mentioned operating part 9 and is provided at the end with a connector 14 connected to the above-mentioned light source apparatus 2. Also, the above-mentioned connector 14 and video processor 3 are connected with each other through a scope cable 15.

Figure 2:
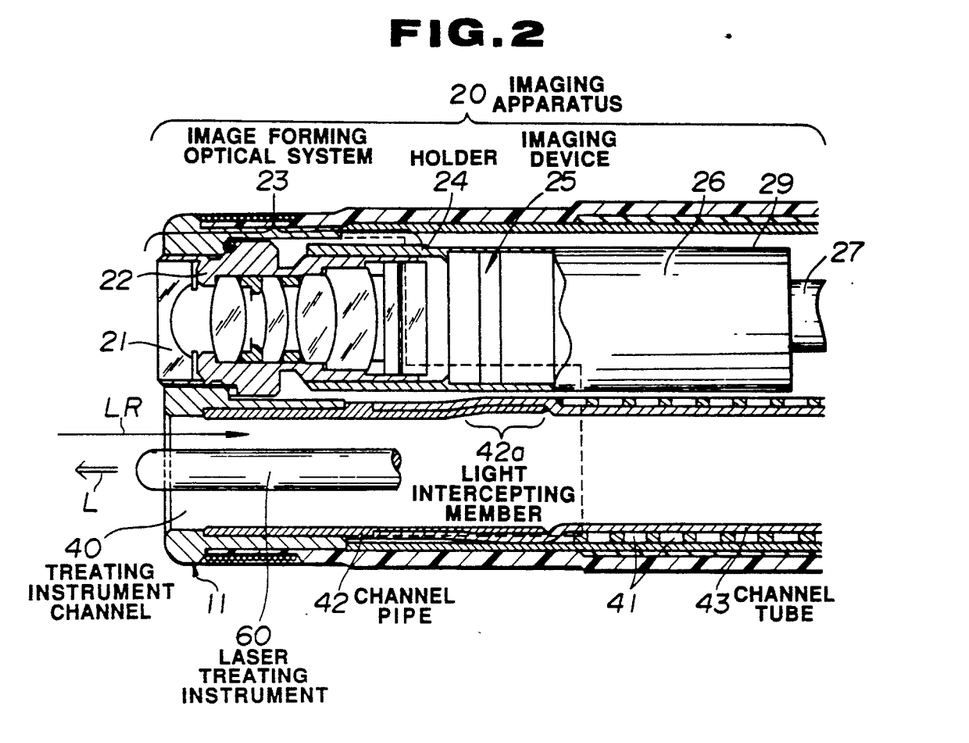
FIG. 2 is a sectioned view showing an endoscope tip.
Figure 3:
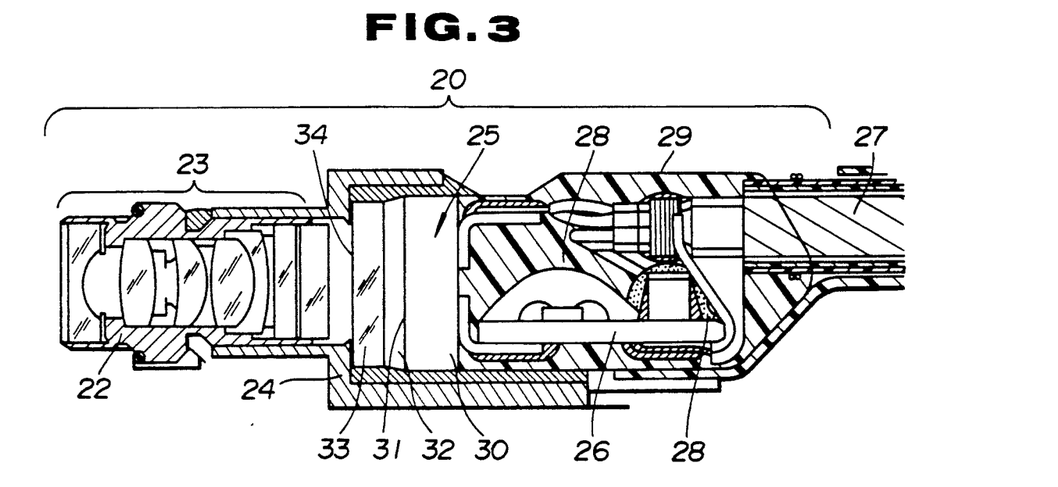
FIG. 3 is a sectioned view showing an imaging apparatus.
Figure 4:
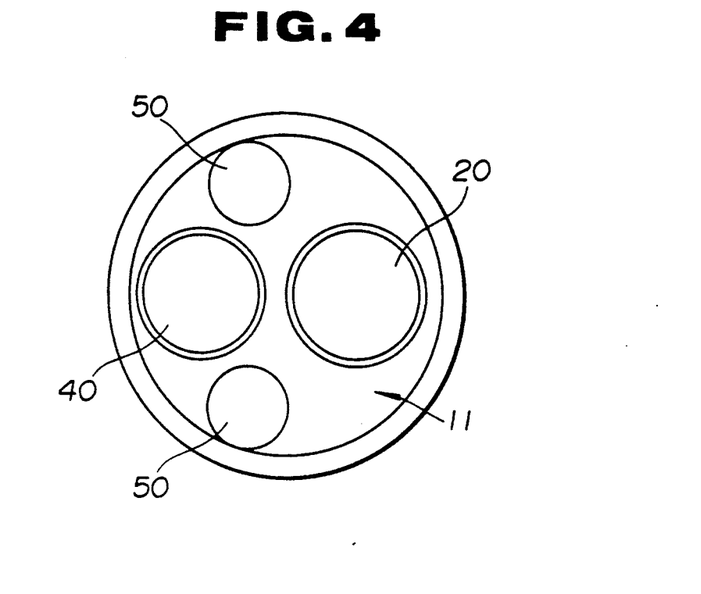
FIG. 4 is an elevation of the tip.

As shown in FIGS. 2 to 4, the video endoscope 1 is provided in the insertable part 8 at the tip in parallel with an imaging apparatus 20 photoelectrically converting an optical image of an object part to an imaging signal, a treating instrument channel 40 through which a laser treating instrument is passed and an illuminating optical system 50 consisting of a light guide fiber bundle leading an illuminating light illuminating the part to be inspected and an illuminating window. The imaging apparatus 20 is provided with an image forming optical system 23 fixed with a lens frame 22 and arranged on the operating part side of the observing window 21 and a solid state imaging device 25 fixed with a solid state imaging device holder 24 and solid state imaging device driving circuit 26 further on the operating part side of the image forming optical system 23. A cable 27 is pulled out of the solid state imaging device driving circuit 26. The solid state imaging device holder 24 is formed of copper or stainless steel so as to transmit no laser light. Also, the imaging apparatus 20 is covered from the solid state imaging device 25 to the cable with a bonding material 28 and thermoshrinking tube 29 to maintain the strength such parts. The solid state imaging device 25 is sealed on a light receiving surface 31 on a base member 30 with a transparent resin 32 and transparent glass 33 and has an incident surface 34 connected with the image forming optical system 23 or lens frame 22 so as to be integrally formed. As shown in FIG. 2, a channel tube 43 forming a treating instrument channel 40 arranged near the solid state imaging device 25 is fitted on the outer periphery with a channel coil 41 to prevent buckling. On the other hand, a channel pipe 42 made, for example, of stainless steel is connected to this channel tube 43 at the tip so as to be connected with the tip 11.

In this first embodiment, the above mentioned channel pipe 42 made, for example, of stainless steel transmitting no laser light is extended at the ending end to the operating side from the light receiving part 31 of the solid state imaging device 25 to make a light shielding part 42a so as to intercept laser light leaking from the laser treating instrument and a reflected laser light entering the above mentioned light receiving part 31 through a course other than the optical course leading to the light receiving surface 31 of the solid state imaging device 25 through the image forming optical system 23 from the above mentioned observing window 21.

The operation of the thus formed embodiment shall be explained in the following.

Here, the laser light is such laser light utilized by a laser treating instrument used in an endoscope as, for example, in the following:
1) Argon laser (Wavelength: 488 nm).
2) YAG laser (Wavelength: 1060, 1320 nm).
3) CO laser (Wavelength: 5.3, 5 to 7 $\mu$m).
4) $CO_2$ laser (Wavelength: 10.6 $\mu$m).
5) He-Ne laser (Wavelength: 504, 604, 612, 638, 1152, 153, 3391 nm).
6) Dye laser (Wavelength: 300 to 1000 nm)

In this first embodiment, the above mentioned various laser lights can be intercepted by the channel pipe (light shielding part 42a) 42.

When a laser probe (laser treating instrument) 60 is inserted through the treating instrument channel 40 to make a laser cauterization, a laser light leaking from the laser treating instrument 60 emitting a laser light L and a reflected laser light LR will tend to enter the imaging apparatus 20 through (the bonding material) between the channel tube 43 and channel coil 41. However, because the light shielding part 42a which is the extended part of the channel pipe 42 is provided up to the operating member side of the solid state imaging device 25, the leaking light of the laser light L and reflected laser light LR will be intercepted from entering the light receiving surface 31 of the solid state imaging device 25 through a course other than the optical course leading to the light receiving surface 31 of the solid state imaging device 25 through the image forming optical system 23 from the above mentioned observing window 21.

According to such embodiment, the endoscope image will not be disturbed and the treating operation will not be influenced by the blacking, flare and blooming of the monitor image and therefore will be able to be made accurately and positively.

Figure 5:
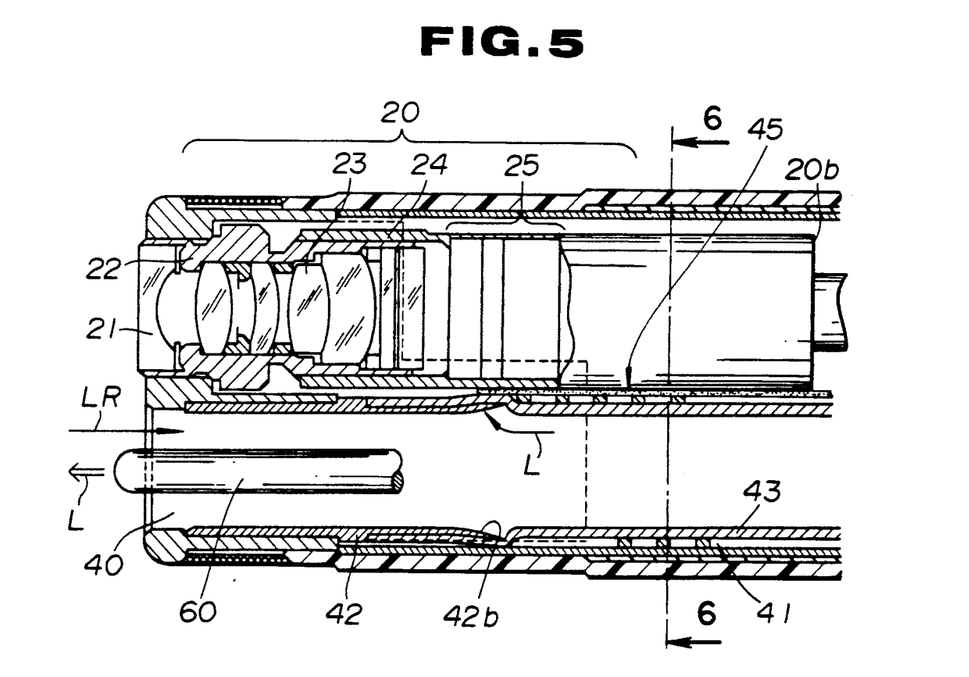
FIG. 5 is a sectioned view showing the second embodiment.
Figure 6:
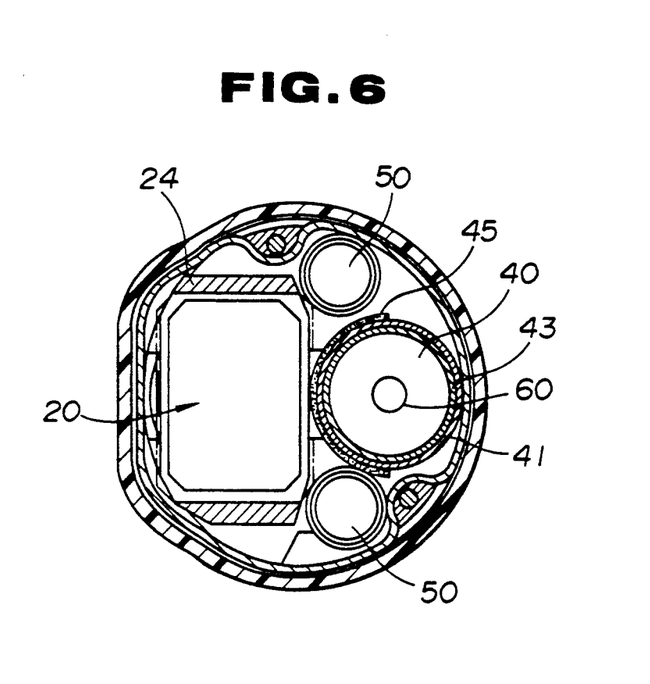
FIG. 6 is a sectioned view on line A—A in FIG. 5.
Figure 7:
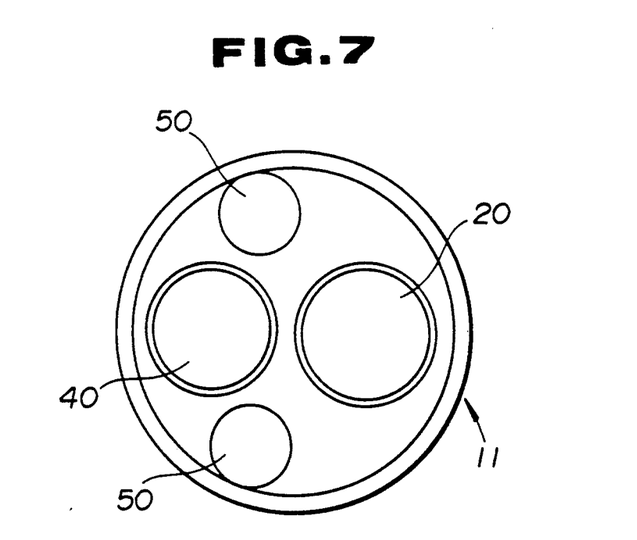
FIG. 7 is an elevation of the tip of the second embodiment.

FIGS. 5 to 7 relate to the second embodiment of the present invention. FIG. 5 is a sectioned view showing a tip of the second embodiment of a video endoscope. FIG. 6 is a sectioned view on line A—A in FIG. 5. FIG. 7 is an elevation of the tip of the embodiment. In these drawings, the same components as of the first embodiment shall bear the same reference numerals and shall not be explained here.

In such second embodiment as is shown in these drawings, light shielding part 45 made of a stainless steel, black ceramics or black organic substance of a thickness, for example, of 0.02 mm is pasted or wound onto a channel tube 43 from the ending end 42b of a channel pipe 42 to the ending end of an imaging apparatus 20 on a half at least on the peripheral side of the solid state imaging device 25 side of the channel tube 43 and channel pipe 42.

The operation of the second embodiment of such formation shall be explained in the following. When a laser probe (laser treating instrument) 60 is inserted through the treating instrument inserting port 12 to make laser cauterization, leaking light from the laser treating instrument 60 emitting a laser light L and a reflected laser light LR will tend to enter the imaging apparatus 20 through (the bonding material) between the channel tube 43 and channel coil 41. However, as the foil as an example of the light shielding part 45 is provided on the channel tube 43 from the ending end 42b of the channel pipe 42 to the ending end of the imaging apparatus 20, the leaking laser light and reflected laser light LR will be intercepted and will not enter the light receiving surface 31 of the solid state imaging device 25.

According to such formation, the endoscope image will not be disturbed and the treating operation will not be influenced by the blacking, flare and blooming of the monitor image and therefore will be able to be made accurately and positively. Also, because such light shielding part 45 is a foil provided on the channel tube 43, the number of steps of working materials will be small.

Figure 8:
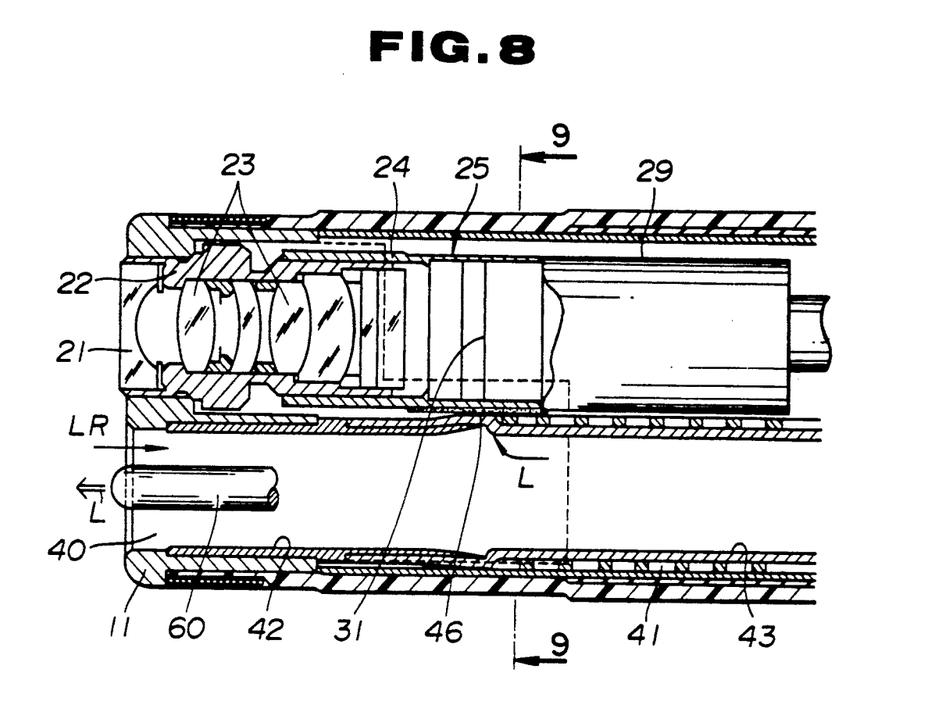
FIG. 8 is a sectioned view of the third embodiment.
Figure 9:
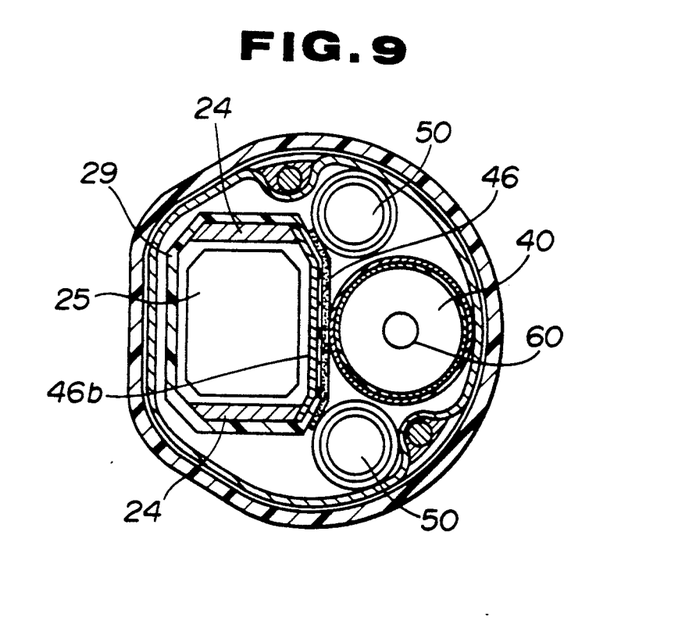
FIG. 9 is a sectioned view on line B—B in FIG. 8.

FIGS. 8 and 9 relate to the third embodiment of the present invention. FIG. 8 is a horizontally sectioned view of the third embodiment. FIG. 9 is a sectioned view on line B—B in FIG. 8. In these drawings, the same components as of the first embodiment shall bear the same reference numerals and shall not be explained here.

In the third embodiment shown in these drawings, a light shielding part 46 made of a foil is pasted so as to cover the side surface side of the light receiving surface 31 onto the side surface at least on the treating instrument channel 40 side of the solid state imaging device 25 housed and protected in the solid state imaging device holder 24. Here, the foil 46 as the light shielding part is pasted onto the side surface of the thermoshrinking tube 29 and solid state imaging device holder 24. By the way, in this embodiment, the foil 46 is pasted onto the side surface of the thermoshrinking tube 29 but, as shown by the hatching in FIG. 9, the foil 46b may be provided between the solid state imaging device 25 and thermoshrinking tube 29.

The operation of the third embodiment of such formation shall be explained in the following. When the laser probe (laser treating instrument) 60 is inserted into the treating instrument channel 40 through the treating instrument inserting port 12 to make a laser cauterization, leaking light of the laser treating instrument emitting a laser light L and a reflected laser light LR will tend to enter the imaging apparatus 20 through a course other than the usual observing light course. However, as foils 46 and 46b are pasted so as to cover the side surface side of the light receiving surface 31 onto the side surface from the thermoshrinking tube 29 to the solid state imaging device holder 24 and on the treating instrument channel 40 side of the solid state imaging device 25 contained in the holder 24, the leaking laser light and reflected laser light will be intercepted and will not enter the light receiving surface 31 of the solid state imaging device 25.

According to such a formation, the endoscope image will not be disturbed and the treating operation will not be influenced by the blacking, flare and blooming of the monitor image and therefore will be able to be made accurately and positively. Also, because the foil 46 is merely pasted onto a predetermined part, the number of steps of working materials will be small.

Figure 10:
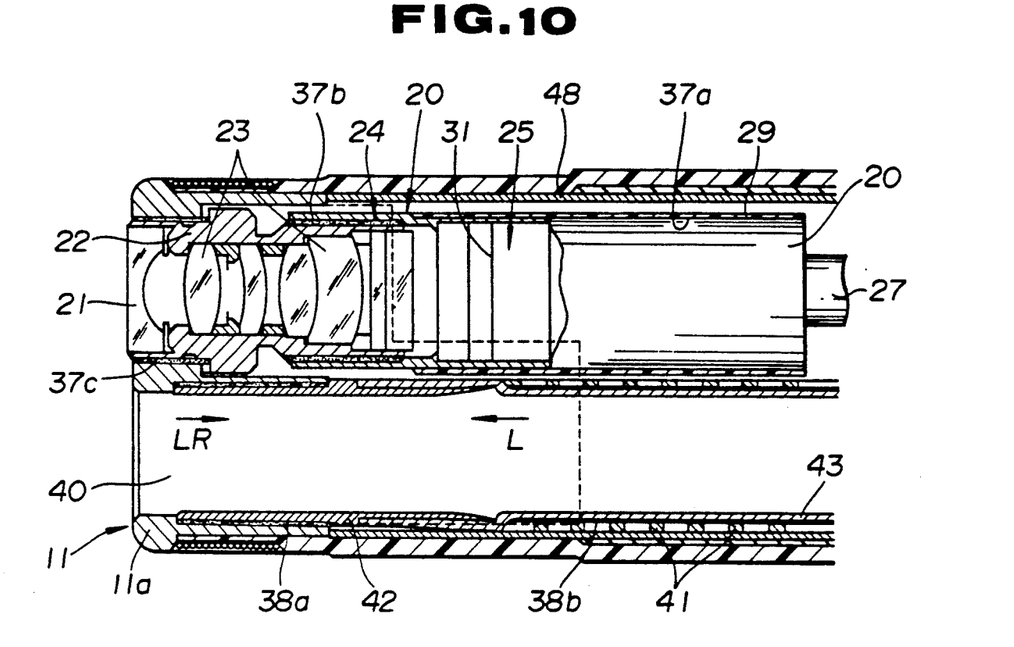
FIGS. 10 and 11 are sectioned views for explaining the fourth and fifth embodiments.
Figure 11:
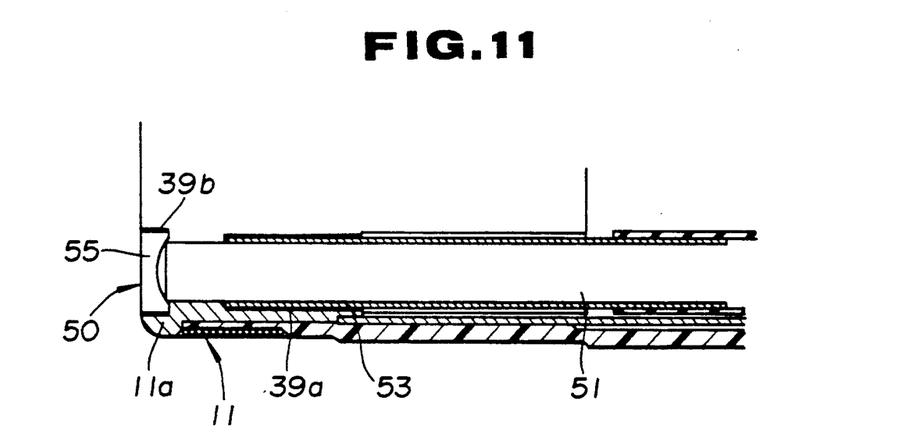

FIGS. 10 and 11 are to explain the fourth embodiment and others following it. FIG. 10 is a sectioned view of a tip. FIG. 11 is a sectioned view of an essential part. In these drawings, the same components. as of the firs t embodiment shall bear the same reference numerals and shall not be explained here.

In a laser therapy, a light shielding part for intercepting leaking light of a laser light L and a reflected laser light LR from entering the imaging device through a course than other the observing system course is formed as mentioned below.

The fourth embodiment is characterized in that the tip forming part 11a forming the main body of the tip 11 is formed of such light intercepting material as a surface treated metal, black ceramics or black high molecular weight material.

The fifth embodiment is characterized in that, as shown in FIG. 10, the surface of the channel pipe 42 is formed of such light intercepting material as a black treated metal or black high molecular weight material.

The sixth embodiment is characterized in that, as shown in FIG. 10, the bending frame 48 is treated to be black inside.

Also, by the above mentioned respective embodiments, leaking light of a laser light L and a reflected laser light LR can be intercepted from entering the light receiving surface 31 of the solid state imaging device 25 through a course other than the ordinary observing system course so that the treating operation may not be influenced by the blacking, flare and blooming of the monitor image.

The seventh embodiment is characterized in that, as shown in FIG. 10, the thermoshrinking tube 29 covering the imaging apparatus 20 is made black.

The eighth embodiment is characterized in that, as shown in FIG. 10, the channel tube 43 is treated to be black or is treated to be black both inside and outside.

Also, by the above mentioned respective embodiment, leaking light of a laser light L and a reflected laser light LR entering the light receiving surface of solid state imaging device through the a course other than the ordinary observing system course can be absorbed so that the treating operation may not be influenced by the blacking, flare and blooming of the monitor image.

The ninth embodiment is characterized in that, as shown in FIG. 10, a black bonding material 37a is used to bond the interior of the imaging apparatus 20.

The tenth embodiment is characterized in that, as shown in FIG. 10, the lens frame 22 and solid state imaging device holder 24 are bonded with each other with a black bonding material 37b.

The 11th embodiment is characterized in that, as shown in FIG. 10, a black bonding material is used to bond the lens frame 22 and tip forming part 11a with each other.

The 12th embodiment is characterized in that, as shown in FIG. 10, the channel pipe 42 and tip forming part 11a are bonded with each other with a black bonding material 38a.

The 13th embodiment is characterized in that, as shown in FIG. 10, a black bonding material 38b is used to bond the channel coil 41 and channel tube 43 with each other.

The 14th embodiment is characterized in that, as shown in FIG. 11, a black bonding material 39a is used to bond the pipe 51 of the light guide fiber bundle 51 and the tip forming part 11a with each other.

The 15th embodiment is characterized in that, as shown in FIG. 11, a black bonding material 39b is used to bond the light guide lens 55 and tip forming part 11a with each other.

Also, by the above mentioned respective embodiments, a light shielding member is arranged in another course through which the laser lights are likely to enter the light receiving surface 31 of the solid state imaging device 25 other than the ordinary observing system course, so that a leaking light of a laser light L and a reflected laser light LR may be absorbed and the treating operation may not be influenced by the blacking, flare and blooming of the monitor image.

That is to say, according to the above mentioned fourth to 15th embodiments, the member and bonding material of the part to be the other course through which a leaking light of a laser light L and a reflected laser light LR are likely to enter the solid state imaging device 25 than the ordinary observing system course are made black to absorb the above mentioned laser lights so as not to reach the solid state imaging device 25.

Thereby, the same as in the second embodiment, a leaking light of a laser light L and a reflected laser light LR will not enter the light receiving surface of the solid state imaging device 25 through the other course than the ordinary observing system course.

It is apparent that, in this invention, working modes different in a wide range can be formed on the basis of this invention without deviating from the spirit and scope of the invention. This invention is not restricted by its specific working mode except being limited by the appended claims.

What is claimed is:

1. In a video endoscope including an insertable part at the tip in parallel with an imaging apparatus, the imaging apparatus including an observing window, imaging forming optical system and solid-state imaging device and a treating instrument channel through which a laser treating instrument is insertable, the improvement comprising:
a light intercepting means for intercepting laser light leaking from said laser treating instrument inserted through said treating instrument channel and from reflected laser light so as not to enter a light receiving part of said solid-state imaging device through a course other than an axially-oriented optical course leading to said light receiving part of said solid-state imaging device through said image forming optical system from said observing window.

2. A video endoscope according to claim 1, wherein a course other than the optical course leading to said light receiving part of the said solid-state imaging device through said image forming optical system from said observing window is a course leading to a side of said imaging apparatus from a peripheral wall of said treating instrument channel.

3. A video endoscope according to claim 1, wherein said light intercepting means forms a tip side of said treating instrument channel and a channel pipe connected to a channel tube is formed of a material not transmitting a laser light and is extended at an end rearward from said light receiving part of said solid state imaging device.

4. A video endoscope according to claim 1, wherein said light intercepting means is arranged at least on a peripheral half of said solid state imaging device side from an end of said channel pipe forming said treating instrument channel to the vicinity of said imaging apparatus ending end of said channel tube.

5. A video endoscope according to claim 4, wherein said light intercepting means is arranged on an outer periphery of said channel tube.

6. A video endoscope according to claim 1, the improvement further comprising:
a holder housing said imaging device within said endoscope; and
a thermoshrinking tube in the rear of said imaging device,
wherein said light intercepting means is arranged on said treating instrument channel side in an area extending from said holder to said thermoshrinking tube.

7. A video endoscope according to claim 6, wherein said light intercepting means comprises a foil blocking the transmission of laser light.

8. A video endoscope according to claim 1, wherein said light intercepting means has a tip forming part forming a main body of said tip of said insertable part formed of a light intercepting material.

9. A video endoscope according to claim 1, wherein said light intercepting means has a channel pipe forming a treating instrument channel formed of a light intercepting material.

10. A video endoscope according to claim 1, wherein said light intercepting means has a bending frame forming a bending part connected to said tip of said insertable part on a rear side formed of a light intercepting material.

11. A video endoscope according to claim 1, wherein said light intercepting means has a thermoshrinking tube covering said imaging device on a rear side formed to be black.

12. A video endoscope according to claim 1, wherein said light intercepting means has a channel tube forming a treating instrument channel treated to be black.

13. A video endoscope according to claim 1, wherein said light intercepting means has a bonding agent with which a part from a rear of said imaging device to a cable is charged made black.

14. A video endoscope according to claim 1, wherein said light intercepting means has a bonding agent bonding a lens frame housing to an objective lens system and a holder housing the imaging device with each other made black.

15. A video endoscope according to claim 1, wherein said light intercepting means has a bonding agent bonding a lens frame and a tip forming part with each other made black.

16. A video endoscope according to claim 1, wherein said light intercepting means has a bonding agent bonding a channel coil wound on an outer periphery of a channel tube to prevent buckling of said tube and a tue with each other made black.

17. A video endoscope according to claim 1, wherein said light intercepting means has a bonding agent bonding a pipe of a light guide fiber bundle and a tip forming part with each other made black.

18. A video endoscope according to claim 1, wherein said light intercepting means has a bonding agent bonding a light guide lens and tip forming part with each other made black.

* * * * *